(12) United States Patent
Ramotowski

(10) Patent No.: US 7,660,693 B2
(45) Date of Patent: Feb. 9, 2010

(54) ACTIVATION ENERGY MEASUREMENT METHOD

(75) Inventor: Thomas S. Ramotowski, Tiverton, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 12/022,415

(22) Filed: Jan. 30, 2008

(65) Prior Publication Data
US 2009/0188333 A1 Jul. 30, 2009

(51) Int. Cl.
*G06F 3/01* (2006.01)
(52) U.S. Cl. .................. 702/127; 702/130; 702/176; 702/182
(58) Field of Classification Search .......... 702/52, 702/65, 81, 104, 127, 136, 184, 185; 204/401; 428/469; 700/291
See application file for complete search history.

(56) References Cited

U.S. PATENT DOCUMENTS

| | | | | |
|---|---|---|---|---|
| 5,942,333 A | * | 8/1999 | Arnett et al. | 428/469 |
| 6,868,310 B2 | * | 3/2005 | Nasman et al. | 700/291 |
| 7,141,150 B1 | * | 11/2006 | Welch et al. | 204/401 |

* cited by examiner

*Primary Examiner*—Eliseo Ramos Feliciano
*Assistant Examiner*—Felix E Suarez
(74) *Attorney, Agent, or Firm*—James M. Kasischke; Michael P. Stanley; Jean-Paul A. Nasser

(57) ABSTRACT

A method for computing activation energy of diffusion for a material in a liquid is provided. At least two identical samples of the material are submerged in the liquid at different temperatures. The time required for each sample to reach a goal weight percentage is measured. A reaction acceleration factor is computed for the two samples from the resulting times and temperatures. Activation energy of diffusion is computed from the reaction acceleration factor and the temperatures. Additional samples can be used to give an error estimate.

12 Claims, No Drawings

ACTIVATION ENERGY MEASUREMENT METHOD

STATEMENT OF GOVERNMENT INTEREST

The invention described herein may be manufactured and used by or for the Government of the United States of America for governmental purposes without the payment of any royalties thereon or therefore.

CROSS REFERENCE TO OTHER PATENT APPLICATIONS

None.

BACKGROUND OF THE INVENTION (1) Field of the Invention

The present invention relates to a material testing method for determining the activation energy for diffusion through polymers.

(2) Description of the Prior Art

Polymer coated material are frequently used in a marine environment. In these materials, a polymer such as a paint or a plastic is painted, coated or formed on a substrate. The polymer acts as a barrier preventing environmental fluids from affecting the substrate. Environmental fluid diffusing through the polymer can result in corrosion or electrical shorting. Thickness of the polymer coating is also of concern for cost, weight and geometric considerations. Thus, there is a great interest in reducing the permeability of polymer materials. This allows a thinner coating of polymer on the substrate to be protected.

Diffusion is also important for maintaining bonding of the polymer coating on the substrate. In cathodic delamination, the current model holds that water and oxygen diffuse through the polymer layer to trigger cathodic delamination. Delamination is begins by the build up of water in the space between the polymer and the substrate. This results in interfacial blisters which triggers the actual delamination or debonding.

Activation energy, $E_a$, is an important value for determining the rate of diffusion. Activation energy is akin to an energy barrier that must be surmounted by the reactants before a reaction can take place. The higher the activation energy, the slower the reaction proceeds at the measured temperature. Unfortunately, activation energy is often unknown for a given material or set of materials, and it requires experimental determination.

Activation energy, $E_a$, is typically calculated by first measuring water diffusion constants at three different temperatures for the polymer in question, and then relating them to the Arrhenius equation. This tends to be a time consuming process because the polymer samples must fully saturate with water before calculations can be made. There are also several ways to calculate diffusion coefficients, and the different methods may not produce compatible results.

SUMMARY OF THE INVENTION

An object of this invention is to provide a method for determining the saturation activation energy for a material of interest.

Accordingly, the current invention provides a method for computing activation energy of diffusion for a material in a liquid. At least two identical samples of the material are submerged in the liquid at different temperatures. The time required for saturation of each sample is measured. A reaction acceleration factor is computed for the two samples from the saturation times and temperatures. Activation energy of diffusion is computed from the reaction acceleration factor and the temperatures. Additional samples can be used to give an error estimate.

DESCRIPTION OF THE PREFERRED EMBODIMENT

This invention provides an improved method for measuring the activation energy for diffusion of water through a polymer. This method uses the reaction acceleration factor ("RAF") equation derived from the Arrhenius equation:

$$RAF = e^{\frac{-E_a(T_2-T_1)}{R(T_2T_1)}} \quad (1)$$

where: RAF is the reaction acceleration factor,
$E_a$ is the activation energy,
R is the gas constant, and
$T_1$ and $T_2$ are the absolute temperature in degrees Kelvin of the reactions.

The reaction acceleration factor equation (1) is used to calculate $E_a$ for diffusion of water into the polymer of interest. Identical polymer samples are used. 1/16 in. thick, 2 to 3 in. diameter disks are preferred. The samples are divided into at least two groups. The first group is placed into a container filled with distilled water at a first temperature, $T_1$. The other group is placed in distilled water at a different temperature, $T_2$. The mass of each sample is monitored until it becomes saturated with water (i.e., the mass gain levels off). The time required to saturate two identical polymer disks at two different temperatures can be used to determine the RAF for the process by dividing the time $t_1$ required by the first temperature ($T_1$) experiment sample by the time $t_2$ required by the different temperature ($T_2$) experiment sample.

$$RAF = \frac{t_1}{t_2} \quad (2)$$

A third sample or group of samples can be tested at a third temperature or at one of the other temperatures. This sample serves as a control to ensure accuracy. The two temperatures involved are the $T_1$ and $T_2$ values in the RAF equation, which can then be solved for the only remaining variable, $E_a$. (Note, R is a constant.)

$$E_a = \frac{-RT_2T_1(\ln(RAF))}{T_2 - T_1} \quad (3)$$

In an alternative embodiment, activation energy, $E_a$, can be calculated for diffusion of water into a polymer until the sample has reached a predetermined percentage weight gain. As an initial step, a predetermined percentage weight gain must be selected. One practicing this method should insure that the predetermined percentage weight gain is less than the percentage weight gain at saturation. Factors that can be used to determine this predetermined percentage weight gain include equipment accuracy, time available for the test, and accuracy required for the result.

After selecting the percentage weight gain, identical samples are divided into at least two groups. The first group is placed into a container filled with distilled water at a first temperature, $T_1$. The other group is placed in distilled water at a different temperature, $T_2$. The mass of each sample is monitored until it reaches the predetermined percentage weight gain. As above, the time required to saturate two identical polymer disks at two different temperatures can be used to determine the RAF for the process by dividing the time $t_1$ required by the first temperature ($T_1$) experiment sample by the time $t_2$ required by the different temperature ($T_2$) experiment sample. A third group of samples can be tested as a control at either $T_1$, $T_2$, or a third temperature, $T_3$, until it reaches the predetermined percentage weight gain. Activation energy, $E_a$, is calculated as given in Equation (3), above.

These embodiments provide a more direct way to calculate $E_a$ for the diffusion through a polymer. This calculation does not depend on additional assumptions in the calculation of diffusion constants. This method can be used to determine the activation energy, $E_a$, when long-term effects of polymer immersion are of interest.

The method taught here can be varied in several respects. The size and shapes of the samples can be different as long as all of the samples tested for a given material are identical. The values of $T_1$ and $T_2$ can be varied. Different fluids can be used as the testing environment.

In light of the above, it is therefore understood that within the scope of the appended claims, the invention may be practiced otherwise than as specifically described.

What is claimed is:

1. A method for computing activation energy of diffusion for a material of interest in a liquid of interest comprising the steps of:
    preparing at least two identical samples of said material of interest;
    placing a first sample of said at least two identical samples in the liquid of interest at a first temperature;
    measuring the length of time required to saturate said first sample with said liquid of interest to obtain a first saturation time;
    placing a second sample of said at least two identical samples in the liquid of interest at a second temperature different from said first temperature;
    measuring the length of time required to saturate said second sample with said liquid of interest to obtain a second saturation time;
    computing a reaction acceleration factor by dividing said first saturation time by said second saturation time;
    and computing an activation energy using said reaction acceleration factor, said first temperature and said second temperature.

2. The method of claim 1 wherein said step of computing an activation energy is performed using the Arrhenius equation.

3. The method of claim 1 further comprising the steps of:
    preparing a third sample of the material of interest, said third sample being identical to said first sample and said second sample;
    placing said third sample in a container filled with the liquid of interest at a third temperature;
    measuring the length of time required to saturate said third sample with said liquid of interest to obtain a third saturation time; and
    calculating the error for said computed activation energy using said third saturation time and said computed activation energy.

4. The method of claim 3 wherein said third temperature is a selected one of said first temperature and said second temperature.

5. The method of claim 1 where the liquid is water.

6. The method of claim 1 wherein the step of measuring the length of time required to saturate one of said samples comprises:
    weighing said sample at different times after said step of placing in the liquid of interest;
    recording the measured weight after each step of weighing; and
    identifying the time at which said measured weight stops increasing as the length of time required to saturate said sample.

7. A method for computing activation energy of diffusion for a material of interest in a liquid of interest comprising the steps of:
    preparing at least two identical samples of said material of interest;
    determining a goal percentage weight gain;
    placing a first sample of said at least two identical samples in the liquid of interest at a first temperature;
    measuring the length of time required for said first sample to reach said goal percentage weight gain after being placed in said liquid of interest to obtain a first time;
    placing a second sample of said at least two identical samples in the liquid of interest at a second temperature different from said first temperature;
    measuring the length of time required for said second sample to reach said goal percentage weight gain after being placed in said liquid of interest to obtain a second time;
    computing a reaction acceleration factor by dividing said first time by said second time; and
    computing an activation energy using said reaction acceleration factor, said first temperature and said second temperature.

8. The method of claim 7 wherein said step of computing an activation energy is performed using the Arrhenius equation.

9. The method of claim 7 further comprising the steps of:
    preparing a third sample of the material of interest, said third sample being identical to said first sample and said second sample;
    placing said third sample in the liquid of interest at a third temperature;
    measuring the length of time required for said third sample to reach said goal percentage weight gain after being placed in said liquid of interest to obtain a third time; and
    calculating the error for said computed activation energy using said third time and said computed activation energy.

10. The method of claim 9 wherein said third temperature is a selected one of said first temperature and said second temperature.

11. The method of claim 7 where the liquid is water.

12. The method of claim 7 wherein the step of measuring the length of time required to reach said goal percentage weight gain for one of said samples comprises:
    weighing said sample at different times after said step of placing in the liquid of interest;
    recording the measured weight after each step of weighing; and
    identifying the time at which said measured weight is at least the weight of the sample given by said determined goal percentage weight gain.

* * * * *